United States Patent [19]
Chow et al.

[11] Patent Number: 5,571,285
[45] Date of Patent: Nov. 5, 1996

[54] SURGICAL STAPLE FOR INSERTION INTO TISSUE

[75] Inventors: Hector Chow; Earl J. Mills, both of Cincinnati; Federico Bilotti, Madeira; Ronald J. Brinkerhoff, New Richmond; Martin Madden; Richard L. Grant, both of Cincinnati, all of Ohio

[73] Assignee: Ethicon, Inc., Somerville, N.J.

[21] Appl. No.: 860,479

[22] Filed: Mar. 30, 1992

Related U.S. Application Data

[63] Continuation-in-part of Ser. No. 641,380, Feb. 19, 1991, abandoned.

[51] Int. Cl.⁶ .................................................. A61B 17/00
[52] U.S. Cl. .................................................. 606/219; 606/75
[58] Field of Search ........................ 606/75, 219, 220; 206/339, 340; 227/902

[56] References Cited

U.S. PATENT DOCUMENTS

| | | | |
|---|---|---|---|
| 4,526,174 | 7/1985 | Froehlich | 128/335 |
| 4,809,695 | 3/1989 | Gwathmey et al. | 128/334 R |
| 4,848,637 | 7/1989 | Pruitt | 227/19 |
| 4,930,503 | 6/1990 | Pruitt | 227/178 |
| 4,941,623 | 7/1990 | Pruitt | 227/19 |

FOREIGN PATENT DOCUMENTS

| | | |
|---|---|---|
| 0283127 | 9/1988 | European Pat. Off. |
| 2233903 | 1/1991 | United Kingdom |

*Primary Examiner*—Sam Rimell
*Attorney, Agent, or Firm*—Paul A. Coletti

[57] ABSTRACT

A new method is shown whereby staples are closed to smaller heights so that virtually total hemostasis is possible. Also, the staple legs in alternate rows in the surgical stapler are made to interlock so that during closure, hemostasis is effected by the interlocking of the staple legs.

9 Claims, 4 Drawing Sheets

5,571,285

SURGICAL STAPLE FOR INSERTION INTO TISSUE

FIELD OF THE INVENTION

This application is a continuation-in-part of Ser. No. 641,380, filed Feb. 19, 1991, now abandoned.

This invention relates to a surgical staple for insertion into tissue. More specifically, the invention relates to the use in the mesentery of a patient of rows of staples where each of the staples has a crown and a pair of legs such that the legs overlap each other along their ends. More specifically, it relates to a stapler for applying two, three, or four rows of staples with at least one row containing such flattened staples, and designed to be applied to the tissue of the mesentery such that blood flow is sealed off. Even more specifically, it applies to a method for applying surgical staples wherein the folded staple legs of a row of staples interlock with the folded staple legs of an adjacent row of staples.

BACKGROUND OF THE INVENTION

The stomach, appendix, jejunum, ileum, ascending colon, transverse colon, descending colon, liver and spleen are internal organs associated with the gastro intestional tract. Some or all of the structures are totally or partially suspended by mesenteries which also contain blood vessels, lymphatics and lymph nodes. The mesenteries vary in thickness, but all contain fatty tissue and blood vessels which vary in size from 1.0 cm. in diameter down to less than 0.1 mm. in diameter. The greater omentum is a double fold of mesentery and it too carries large numbers of blood vessels of varying size, and the thickness of the greater omentum is quite variable from one patient to another.

There are stapling devices for closing the bronchus, pulmonary artery, pulmonary veins, for closure of the large or small intestine, for closure of the stomach or stapling of the stomach, for end-to-end anastomosis of the intestines, for side-to-side anastomosis of the intestines and for individual ligation and for division of a blood vessel. In addition, there are a variety of occluding clips for blood vessels and skin staplers. Because of the fatty tissue and the variety of sizes of blood vessels present in the mesentery and the omentum, the available staplers are not satisfactory for stapling the mesentery and the omentum. Current appliers ligate only one or a few vessels at a time and commonly tear blood vessels in the vicinity of their use, requiring time consuming repairs after ligation of the intended vessel.

Pruitt, U.S. Pat. No. 4,848,637 and Pruitt, U.S. Pat. No. 4,930,503 describe process, stapler and cartridge suitable for stapling the mesentery and the omentum using three or more rows of staples having different crown size in at least one row of staples as compared to the other row of staples, including an arrangement of staples in which the crown sizes of alternate staples in the same row differ from crown size of the staples between said alternate staples. This arrangement is based on the fact that the staples having larger crowns also have longer prongs (or legs) and the staples having smaller crowns have shorter prongs. This is based on the fact that the prong size is determined by the requirement to reach halfway across the bottom of the crown and also to have enough additional length to form a loop under the crown. This loop serves a similar function as a stitch in a suture or ligation used to seal off the blood vessels after an incision has been made in human tissue. The larger the loop is to be, the greater will the length of the prong be in excess of that required to reach one-half the length of the crown. With mesentery and omentum a combination of large loops and smaller loops is desired to seal off the flow of blood from the blood vessels severed by the incision. Advantageously each blood vessel and also some fatty tissue to squeeze the blood vessel shut is embraced by a loop of the staple.

When the crown sizes are the same in a number of rows of staples, as provided in commercially available cartridges of staples, the staples in one row are staggered with respect to the staples in the adjacent row or rows. The staggering in each case is effected by positioning the beginning end of the first staple in the second row of staples opposite the midpoint of the first staple of the first row of staples. This means that the midpoint of each of the staples in the second row of staples is opposite a gap between staples in the first row. It also means that the gaps between the staples in the second row are opposite the midpoint of adjacent staples in the first row. The midpoint of the staples is where the ends of the prongs on the underside of those staples come near each other and in many cases leave a gap between each other and between the prong ends and the crown. In some cases, the curvature at the end of a closed staple leg is formed such that a space exists between formed legs. These conditions mean that blood vessels which come in the gaps between staples in one row will not be encased in a loop in the adjacent row of staples.

In Pruitt, U.S. Pat. No. 4,941,623, a process, a stapler and a staple cartridge are disclosed suitable for use on the mesentery and on the omentum, the use of which process, stapler and cartridge are capable of effectively stopping the bleeding of blood vessels in that part of the mesentery or of the omentum which is being resected. These are designed to apply three or more rows of staples of the same size "crown" or main body portion of the staples, the rows being substantially parallel to each other and the staples in each row being staggered one-quarter of the crown length with the staples in the adjacent row or rows of staples. There is at least one row in which the prong lengths of the staples differ from the length of the staple prongs in the other row or rows.

SUMMARY OF THE INVENTION

It is an object of this invention to provide a process for effectively stapling the mesentery and the omentum.

It is an object of this invention to provide a stapler and a cartridge therefore which is suitable for stapling the mesentery and the omentum.

It is also an object of this invention to provide a stapling device with appropriate arrangement of staples which will satisfactorily seal off blood vessels of varying sizes as found in the mesentery and in the omentum.

It is also an object of this invention to provide an arrangement of staples which provide tighter closure of typical surgical staples.

It is yet another object of the invention to provide closure of staples wherein adjacent rows seal with one another.

It is still another object of the invention to provide a staple cartridge in which these staples rows adequately hold the mesentery or other tissue closed.

Other objects of the invention are accomplished in the surgical staple with a crown connected to two legs wherein the staple in its closed tissue gripping position comprises the legs folded toward the crown so that the leg ends approximate the crown. Furthermore, the leg ends overlap one another along the length of the crown. Ideally, each of these surgical staples are contained in a row of staples in a surgical staple cartridge. Each row of these staples contains staples of the same dimensions where some of the rows contain staples formed in such a flattened fashion. In other embodiments there are disclosed two adjacent rows of staples where such flatter type of staples are disclosed. Finally, the staples are disclosed such that they are displaced at an angle within the cartridge. This causes the staples to be tilted so that the legs of the staples are caused to be engaged within the rows of the adjacent staple legs upon forming. Thus, the legs in the row of staples are intertwined with the legs of the adjacent rows creating better closure of the mesentery.

These and other objects are more clearly described in the attached drawings and the detailed description which follow.

DETAILED DESCRIPTION OF THE DRAWINGS

DETAILED DESCRIPTION OF THE INVENTION

Figure 1:
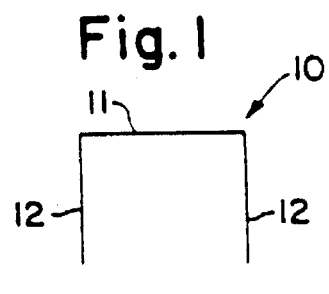
FIG. 1 is an elevation view of a typical surgical staple.

As seen in FIG. 1, a typical surgical staple 10 has a crown 11 attached to two sharpened legs 12. Generally in preformed state, these legs 12 are perpendicular to crown 11 and legs 12 are of equal length.

Figure 14:
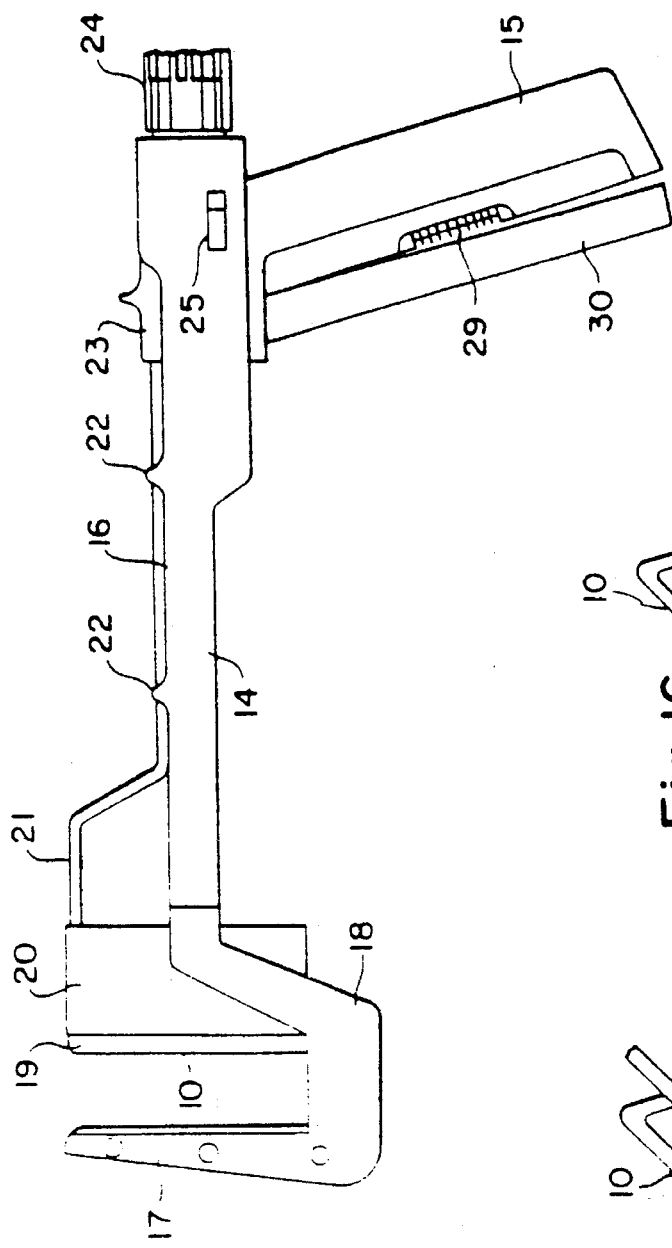
FIG. 14 is a typical linear surgical stapler.

FIG. 14 gives a front elevational view of a surgical stapler 14 of this invention which in part resembles a gun with handle 15, barrel 16 and trigger 30. Safety guard 29 is shown in retracted position. Anvil 17 is supported by arm 18 extending from the forward or front end of barrel 16. Staple cartridge 19 is supported by cartridge holder 20. Legs 11 of staples 10 are inside the cartridge 19 and are not visible in this view. Positioning rod 21 passes through an opening extending through cartridge holder 20 and also through guides 22 and 22. Knob 23 is fastened to the back end of rod 21 and may advance the forward end of rod 21 to the anvil by pushing knob 23 forward and may retract the rod 21 away from the anvil by pushing knob 23 backward. Cartridge 19 is connected by an arm (not shown here) extending inside barrel 16 and is connected indirectly to knob 24. Knob 24 is capable by a screw arrangement not shown to advance and retract the cartridge and cartridge holder. Axial rotation in a clockwise direction advances the cartridge holder and cartridge toward the anvil and counterclockwise rotation retracts these away from the anvil. Gap setting 25 allows a measurement of the gap between the anvil and the staple cartridge. Closing of trigger 30 toward handle 15 actuates the forward movement of a plunger to force the staples 10 into the grooves of the anvil.

Figure 2:
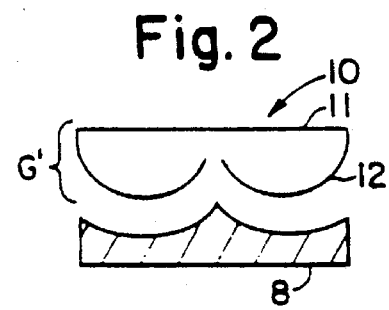
FIG. 2 is a view of a staple formed on a typical anvil.
Figure 3:
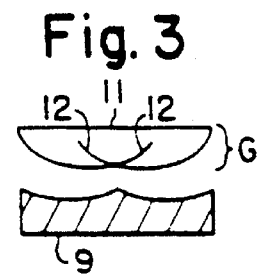
FIG. 3 is a view of a staple of the present invention formed on a modified anvil.

As seen in FIG. 2, the pockets of anvil 8 of a surgical stapler 14 normally form staples 10 so that the legs 12 fold toward the midpoint of the crown 11 so that the legs are folded in a "B" figuration. However, according to the present invention as described by modified anvil 9, as shown in FIG. 3, now forms the staples so that legs 12 can overlap. In fact, the modified anvil 9 causes the legs to be formed such that the legs 12 create an overlap of about a quarter of the surgical staple crown 11. Thus, for a crown which is generally about 2.5 to 4.5 mm, preferably 3 to 4 mm, the overlap runs in the range of about 0.6 mm to 1 mm. Typical prong lengths are selected in accordance with the crown length, and are advantageously in the range of 1 to 6 mm, preferably in the range of 2 to 5 mm. Thus, the gap labeled G' and indicated at the sides of FIG. 2 formed with these staples is typically about twice the size of the gap labeled G as indicated at the side of FIG. 3 formed in staples as in FIG. 2. Generally, this gap G' amounts to about 0.25 to 0.5 mm.

Figure 4:
FIG. 4 is a typical pattern of staples as could applied from the stapler in FIG. 14.

In a surgical stapler 14, as in FIG. 14, there are sometimes placed four parallel rows of staples, which are staggered across tissue as in FIG. 4. A knife blade may optionally be placed down the center of the four rows. One aspect of the current invention is to combine different rows of staples as in FIG. 2 and as in FIG. 3. FIGS. 5 through 13 have been found to advantageously create closure of tissue.

Figure 5:
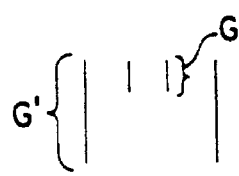
FIG. 5 is a cross-sectional view of an improved pattern of surgical staples.
Figure 6:
FIG. 6, 7, 8, 9, 10, 11, 12 and 13 are typical patterns of surgical staples as in the present invention.
Figure 7:

As seen in FIG. 5, the outer rows of staples have been formed with a gap G', as in FIG. 2; the inner rows of staples have been formed with a gap G, as in FIG. 3. The mechanism for making closure with the inner stapler rows being tighter, causes the outer portions of tissue to be much more exposed to rapid healing in comparison to the inner two rows of tissues, which are tightly closed. The effects of FIGS. 6 and 7 are virtually the same on a closed strip of tissue. Generally, these situations will be selected where it is desirable to get greater closure either to the right or left side of the staple line.

Figure 8:
Figure 9:
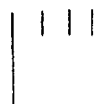
Figure 10:
Figure 11:
Figure 12:
Figure 13:

If it is desired to entirely close off the row of tissue held between the row of staples, it may be desirable to place down a row of staples as in FIG. 8, where tight closure is made in each of the rows of staples. Alternately, an arrangement where three flattened rows are placed down such as in FIGS. 9 or 13 is also effective. Finally, where closure is not the major concern, and yet is necessary, it may be advisable to place down a row of staples where only one staple row is tightly closed, as in FIGS. 10 and 12.

It has been found that each of these configurations as described in the previous specification and figures effects a better hemostasis. This is due, it is believed for a number of reasons. First, it is believed that because there is a variation of rows of tightly closed and less tightly closed tissue, there is not the risk of necrosis of the tissue which may be encountered upon closure which is excessively tight. However, because the tissue is closed tightly in some rows, and is loosely closed in others, it is believed that it is virtually impossible for blood to pass through these tightly and loosely closed rows of tissue. Therefore, such configurations lend to better hemostasis, and therefore improved wound healing after surgical stapling.

Figure 16:
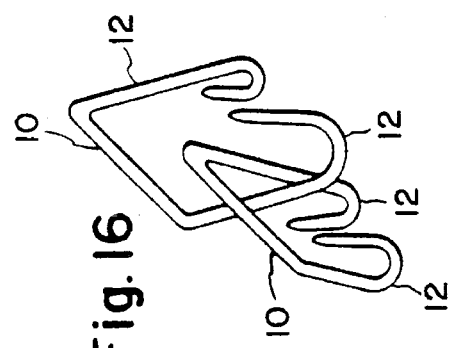
Figure 15:
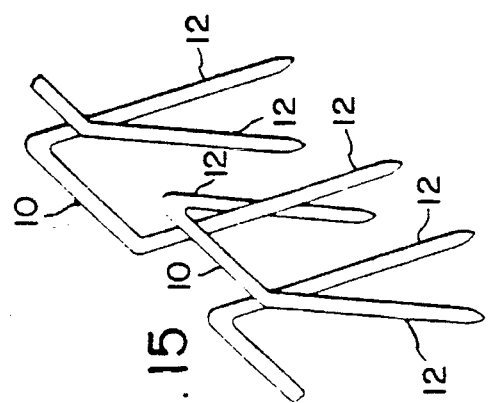
FIG. 15 is a new way of applying rows of surgical staples, as shown in final form in FIG. 16.

Finally, as seen in FIGS. 15 and 16, it may be desirable in addition to the tight closure of each of the staples, to have the staples 10 interlock.

Accordingly, even though the staples 10 are placed down in generally parallel rows, it may be desirable to have the staple legs placed so that they are aligned with a plane which intersects with the plane of the staple cartridge. This can best be seen in FIG. 15, where the staples have been ejected from the cartridge and now are driven along such an intersecting plane so that at least one, and perhaps each, of the rows of staples 10 face another row. In this way, after the staple legs 12 are closed, the staple legs 12 interlock, as seen in FIG. 16. Of course if the staples are tightly locked, as in using the anvils as seen in FIG. 3, closure is virtually continuous. Hemostatic seal in the tissue is assured, and yet the desired flexibility of the stapled tissue still exists.

Figure 17:
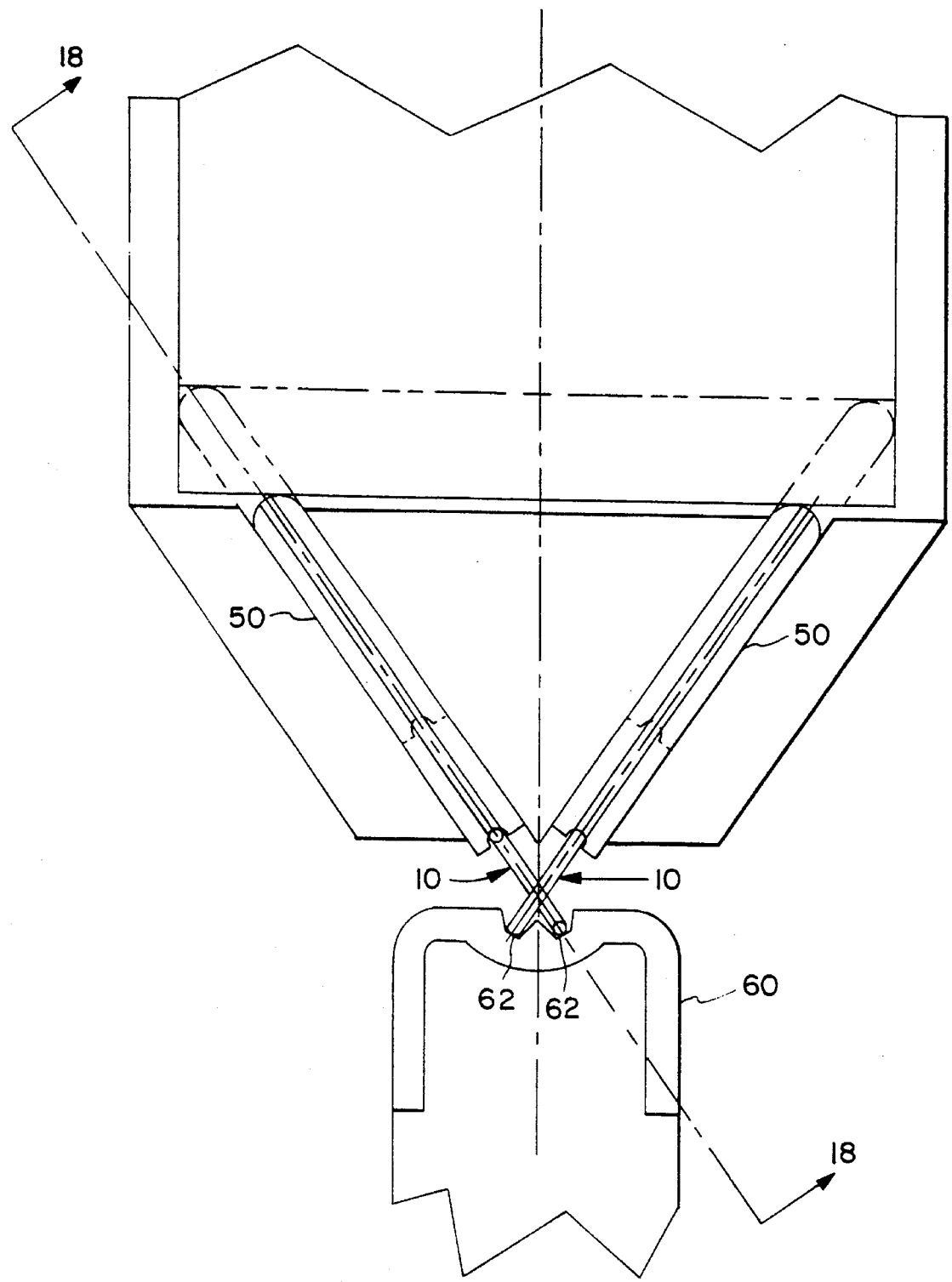
FIG. 17 is a cross-section of an alternate embodiment of a cartridge and stapler arrangement as taken across line 17—17 of FIG. 14.
Figure 18:
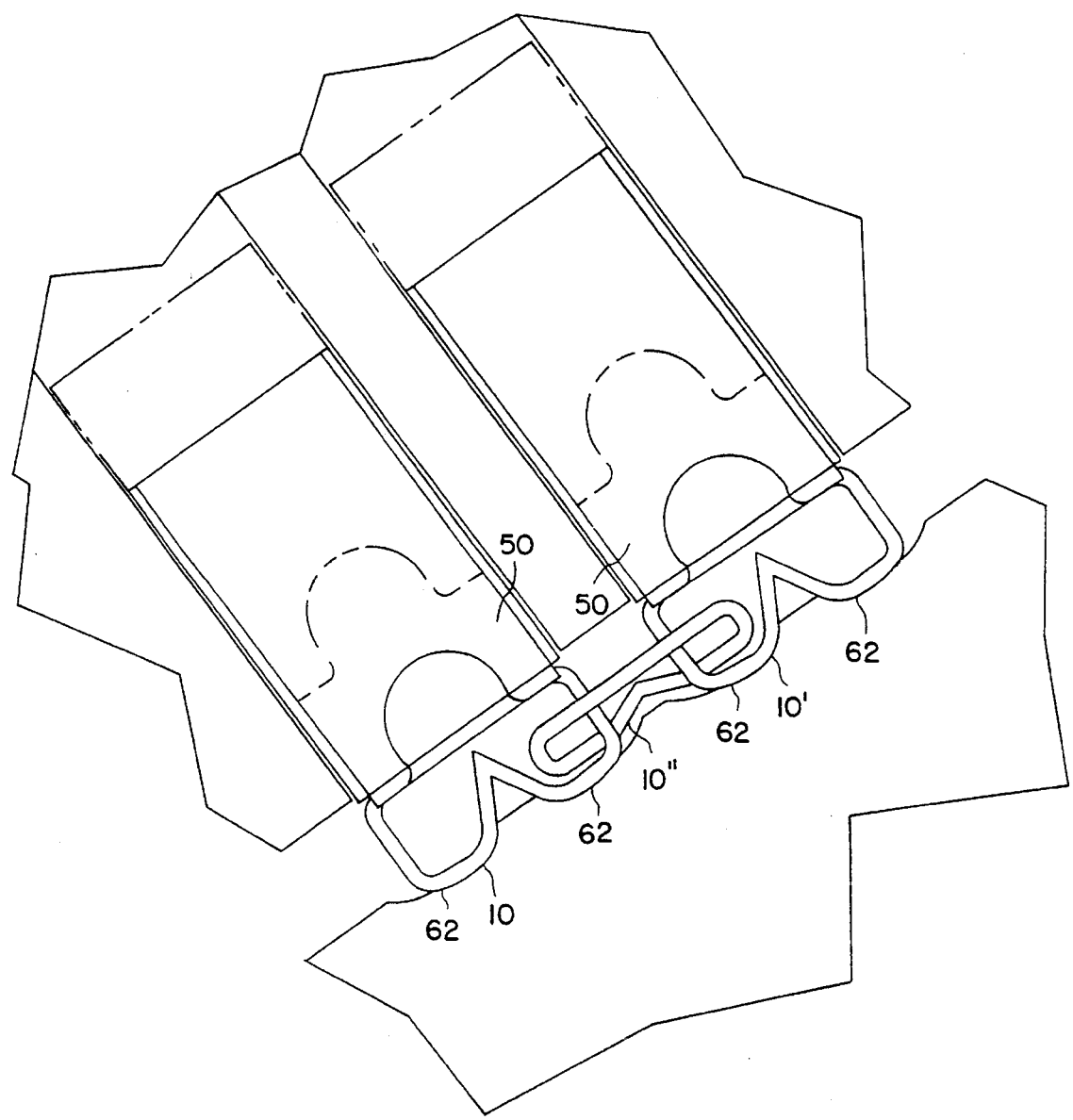
FIG. 18 is a cross-sectional view across lines 18—18 of FIG. 16.

Alternately, as seen in FIGS. 17 and 18 the stapler of FIG. 14 can be configured with a new embodiment in order to effect similar stapler interlocking as described above. There, as is FIG. 17, there is described a stapler anvil configuration wherein the drivers 50 are seen engaging each of the staples 10. These drivers 50 are able to engage the staples through tissue and into an anvil 60 which is seen below the tissue. This anvil 60 has a double pair of pockets 62. Each of the pockets are able to alternately encounter tissue and staples closed from an opposite row. Therefore, interlocking is affected, and seen in the cross-sectional view of the staples in FIG. 18. In fact, as seen in FIG. 18, there is described three interlocking staples 10, 10', 10" wherein the central staple 10" (from an opposite row) is closed more tightly than the adjacent row. This is in keeping with the embodiments described in FIGS. 1-13, and therefore allows in this configuration of the stapler alternate tightly and loosely closed rows of tissue. Thus, the interlocking rows and the loose and tightly closed staple rows are both able to be operated by a stapler as in FIG. 14 with a stapling cartridge and closure scheme as in FIG. 17 and 18.

Also, it is realized that such closure therefore capably affects hemostasis and does not cause necrosis of the tissue. Therefore, less trauma is derived in the stapled area, and it is believed that wound healing will occur more quickly. Therefore, this allows for quicker patient recovery and other time, saving benefits, as would be generally expected.

These and other embodiments of the particular invention have been described herein. Of course, other embodiments are intended to be encompassed. For instance, a cartridge of the invention may contain six rows of staples, or an odd number of rows of staples. It is to be understood that the invention is intended to be encompassed by the following claims and their equivalents.

What is claimed is:

1. A cartridge of surgical staple rows, said staple rows tilted within said cartridge and facing an adjacent row, such that when said staples exit said cartridge to grip tissue, each of the legs in each of said staples forming said tilted rows interlock with one of the legs of a staple in said adjacent row.

2. The cartridge of claim 1 wherein there are four rows of staples.

3. The cartridge of claim 2 wherein at least two of said rows contain staples such that said staples are tilted within said cartridge and facing an adjacent row, such that when said staples exit said cartridge to grip tissue, each of the legs in each of said staples forming said tilted row interlock with one of the legs of a staple in said adjacent row.

4. The cartridge of claim 3 wherein said at least two rows are adjacent each other and face each other.

5. The cartridge of claim 3 wherein said at least two rows are the inner two rows of staples, with the outer rows of staples containing staples closed in a different shape.

6. The cartridge of claim 3 wherein said at least two rows form one longitudinal half of the cartridge, and the other longitudinal half of said cartridge contain staples closed in a different shape.

7. The cartridge of claim 1 wherein all of said rows contain staples such that said staples are tilted within said cartridge and facing an adjacent row, such that when said staples exit said cartridge to grip tissue, each of the legs in each of said staples forming said tilted row interlock with one of the legs of a staple in said adjacent row.

8. The cartridge of claim 7 wherein there are two pairs of rows which face each other.

9. A method of tissue closure comprising first placing at least two rows of surgical staples in tissue, each of said staples having staple legs connected by a crown, and then crimping said staples in said tissue such that at least one of the legs in each said staples in one of said rows interlocks with one of the legs of a said staple in said adjacent row.

* * * * *